United States Patent
Chant et al.

(10) Patent No.: US 10,292,930 B2
(45) Date of Patent: May 21, 2019

(54) MASCARA MIXTURE

(71) Applicant: MPLUS COSMETICS S.R.L., Milan (IT)

(72) Inventors: David Chant, Bangkok (TH); Giacomo Marchetti, Crema (IT)

(73) Assignee: MPLUS Cosmetics S.R.L., Milan (IT)

( * ) Notice: Subject to any disclaimer, the term of this patent is extended or adjusted under 35 U.S.C. 154(b) by 0 days.

(21) Appl. No.: 15/962,459

(22) Filed: Apr. 25, 2018

(65) Prior Publication Data

US 2018/0303748 A1    Oct. 25, 2018

Related U.S. Application Data

(60) Provisional application No. 62/489,493, filed on Apr. 25, 2017.

(51) Int. Cl.
| | |
|---|---|
| *A61K 8/92* | (2006.01) |
| *A61Q 1/10* | (2006.01) |
| *A61K 8/81* | (2006.01) |
| *A61K 8/58* | (2006.01) |
| *A61K 8/36* | (2006.01) |
| *A61K 8/34* | (2006.01) |
| *A61K 8/19* | (2006.01) |
| *A61K 8/37* | (2006.01) |
| *A61K 8/06* | (2006.01) |

(52) U.S. Cl.
CPC ............... *A61K 8/925* (2013.01); *A61K 8/19* (2013.01); *A61K 8/345* (2013.01); *A61K 8/361* (2013.01); *A61K 8/375* (2013.01); *A61K 8/585* (2013.01); *A61K 8/8111* (2013.01); *A61K 8/8182* (2013.01); *A61K 8/922* (2013.01); *A61Q 1/10* (2013.01); *A61K 8/062* (2013.01); *A61K 8/064* (2013.01)

(58) Field of Classification Search
None
See application file for complete search history.

(56) References Cited

U.S. PATENT DOCUMENTS

| | | | |
|---|---|---|---|
| 8,029,773 B2 * | 10/2011 | Loginova | A61K 8/8111 424/70.7 |
| 2002/0004036 A1 | 1/2002 | Piot et al. | |
| 2008/0268070 A1 * | 10/2008 | Sanada | A61K 8/987 424/682 |
| 2016/0199290 A1 | 7/2016 | Shao et al. | |
| 2017/0216160 A1 | 8/2017 | Chant et al. | |

FOREIGN PATENT DOCUMENTS

| | | |
|---|---|---|
| EP | 2179721 A1 | 4/2010 |
| WO | WO2013192632 | * 12/2013 |

OTHER PUBLICATIONS

International Search Report and Written Opinion PCT/US2018/0293334 dated Apr. 25, 2018.

* cited by examiner

*Primary Examiner* — Jennifer A Berrios
(74) *Attorney, Agent, or Firm* — Arent Fox LLP

(57) ABSTRACT

The present disclosure relates to methods of preparing cosmetic compositions by mixing together two different mascara formulations. The starting mascara formulations may contain the same or different ingredients, and they may differ in viscosity and/or in the melting points of their ingredients, such as their waxes.

12 Claims, 2 Drawing Sheets x = emulsifiers (PEG-30 DPHS, GmS-SE)

x = emulsifiers (stearic acid, aminomethyl propandiol)

MASCARA MIXTURE

CROSS-REFERENCE TO RELATED APPLICATIONS

This application claims priority to U.S. Patent Application No. 62/489,493, entitled "Mascara Mixture," filed Apr. 25, 2017, which is incorporated herein by reference in its entirety.

BACKGROUND

One the goals of mascara compositions is to deposit a large amount of product on the lashes as quickly as possible, while at the same time keeping the lashes separate. To accomplish this, mascara formulations are generally prepared to have a very creamy, thick texture, normally created by a wax-in-water emulsion. Such mascara formulations are generally homogeneous compositions, where the wax droplets are all the same. However, when the percentage of the wax in the formula is increased too much, the wax droplets connect to each other, forming a network, and the mascara is too hard to achieve a good application.

SUMMARY OF THE INVENTION

The following presents a simplified summary of one or more aspects of the present disclosure in order to provide a basic understanding of such aspects. This summary is not an extensive overview of all contemplated aspects and is intended to neither identify key or critical elements of all aspects nor delineate the scope of any or all aspects. Its purpose is to present some concepts of one or more aspects in a simplified form as a prelude to the more detailed description that is presented later.

In some embodiments, the present disclosure is directed to a method of preparing a cosmetic composition, the method comprising: providing a first mascara formulation having at least one first wax contained therein; providing a second mascara formulation having at least one second wax contained therein, the at least one second wax having a different melting point than that of the at least one first wax; and mixing together the first mascara formulation and the second mascara formulation, at a temperature below the melting point of both the at least one first wax and the at least one second wax.

In another embodiment, the first and second mascara formulations are mixed at a temperature below the melting point of all the ingredients contained within the first and second mascara formulations.

In yet another embodiment, one of the first and second mascara formulations has a higher viscosity than the other of the first and second mascara formulations.

In a further embodiment, each of the first and second mascara formulations contains a water-in-oil emulsifier and an oil-in-water emulsifier.

In some aspects, the water-in-oil emulsifier in each of the first and second mascara formulations is independently one or more of polyglyceryl-3-rice branate, cetearyl alcohol, polyglyceryl-10 stearate, polyglyceryl-6 stearate, hydroxypropyl guar, cetearyl alcohol, glyceryl stearate, PEG-30 dipolyhydroxystearate, PEG-40 stearate, cetearet-20, 165-PEG-100 stearate, and glyceyl stearate.

In some aspects, the oil-in-water emulsifier in each of the first and second mascara formulations is independently one or more of stearic acid with aminomethyl propandiol, stearic acid with sodium hydroxide, GMS, GMS-SE, and potassium cetyl phosphate.

In yet a further embodiment, the first mascara formulation contains both a water-in-oil emulsifier and an oil-in-water emulsifier, and the second mascara formulation contains one or more oil-in-water emulsifiers and does not contain a water-in-oil emulsifier.

In some aspects, the water-in-oil emulsifier is one or more of polyglyceryl-3-rice branate, cetearyl alcohol, polyglyceryl-10 stearate, polyglyceryl-6 stearate, hydroxypropyl guar, cetearyl alcohol, glyceryl stearate, PEG-30 dipolyhydroxystearate, PEG-40 stearate, cetearet-20, 165-PEG-100 stearate, or glyceyl stearate.

In some aspects, the water-in-oil emulsifier is PEG-30-dipolyhydroxystearate.

In some aspects, the oil-in-water emulsifier in each of the first and second mascara formulations is independently one or more of stearic acid with aminomethyl propandiol, stearic acid with sodium hydroxide, GMS, GMS-SE, and potassium cetyl phosphate.

In some aspects, the oil-in-water emulsifier in the first mascara formulation is GMS-SE, and the one or more oil-in-water emulsifiers in the second mascara formulation is stearic acid with aminomethyl propandiol or GMS, or a combination thereof.

In some aspects, the one or more waxes in each of the mascara formulations are independently selected from joba wax, rice wax, carnauba wax, candelilla wax, beeswax, lanolin wax, orange peel wax, Chinese insect wax, ouricury wax, cork fiber wax, sugar cane wax, Japan wax, sumach wax, montan wax, microcrystalline waxes, paraffins, polyethylene waxes, methicones, dimethicones, and simethicones.

In some aspects, the one or more waxes in each of the mascara formulations are independently selected from beeswax, and carnauba wax.

In some aspects, the first mascara formulation comprises: a phase A comprising: 2.00 weight % of VP/Eicosene copolymer, 2.00 weight % of PEG-30 DPHS, 14.00 weight % of GmS SE, 7.00 weight % of cyclopentasiloxane, 2.00 weight % of polybutene, and 6.00 weight % of hydrogenated olive esters; and a phase B comprising: 3.00 weight % of gum acacia, 8.00 weight % of iron oxide, 0.20 weight % of methylparaben, 0.80 weight % of phenoxyethanol, and 55.00 weight % of water; and the second mascara formulation comprises: a phase A comprising: 2.00 weight % of VP/Eicosene copolymer, 7.00 weight % of stearic acid, 10.00 weight % of beeswax, 4.00 weight % of cyclopentasiloxane, 2.00 weight % of polybutene, 1.00 weight % of GMS, 3.00 weight % of synthetic beeswax, 3.00 weight % of carnauba wax; and a phase B comprising: 3.00 weight % of gum acacia, 1.00 weight % of aminomethylpropandiol, 8.00 weight % of iron oxide, 0.20 weight % of methylparaben, 0.80 weight % of phenoxyethanol, and 55.00 weight % of water.

In some aspects, the method further comprises providing a third mascara formulation having at least one third wax contained therein, the at least one third wax having a different melting point than that of the at least one first wax; and mixing together the first and second mascara formulations with the third mascara formulation at a temperature below the melting points of both the at least one first wax and the at least one third wax.

In some aspects, the third mascara formulation comprises: a phase A comprising: 2.00 weight % of VP/Eicosene copolymer, 7.00 weight % of stearic acid, 10.00 weight % of beeswax, 4.00 weight % of cyclopentasiloxane, 2.00 weight % of polybutene, 6.00 weight % of carnauba wax; and a phase B comprising: 3.00 weight % of gum acacia, 2.00 weight % of aminomethylpropandiol, 8.00 weight % of iron oxide, 0.20 weight % of methylparaben, 0.80 weight % of phenoxyethanol, 55.00 weight % of water.

In some aspects, the first mascara formulation comprises: a phase A comprising: 2.00 weight % of VP/Eicosene copolymer, 7.00 weight % of stearic acid, 10.00 weight % of beeswax, 4.00 weight % of cyclopentasiloxane, 2.00 weight % of polybutene, 1.00 weight % of GMS, 3.00 weight % of synthetic beeswax, and 3.00 weight % of carnauba wax; and a phase B comprising: 3.00 weight % of gum acacia, 1.00 weight % of aminomethylpropandiol, 8.00 weight % of iron oxide, 0.20 weight % of methylparaben, 0.80 weight % of phenoxyethanol, 55.00 weight % of water; and the second mascara formulation comprises: a phase A comprising: 2.00 weight % of VP/Eicosene copolymer, 7.00 weight % of stearic acid, 12.00 weight % of beeswax, 4.00 weight % of cyclopentasiloxane, 2.00 weight % of polybutene, 9.00 weight % of carnauba wax; and a phase B comprising: 3.00 weight % of gum acacia, 2.40 weight % of aminomethylpropandiol, 8.00 weight % of iron oxide, 0.20 weight % of methylparaben, 0.80 weight % of phenoxyethanol, and 49.60 weight % of water.

In another embodiment, the present disclosure is directed to a cosmetic composition comprising: 40-80% of a first mascara formulation having at least one first wax contained therein; and 20-50% of a second mascara formulation having at least one second wax contained therein, the at least one second wax having a different melting point than that of the at least one first wax.

In some aspects, the cosmetic composition further comprises 30% of a third mascara formulation having at least one third wax contained therein, the at least one third wax having a different melting point than that of the at least one first wax.

These and other aspects of the invention will become more fully understood upon a review of the detailed description, which follows.

DETAILED DESCRIPTION

Figure 1:
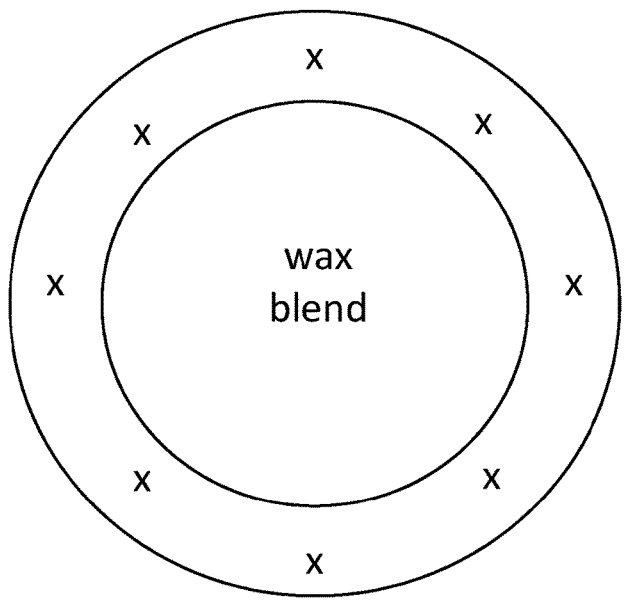
FIGS. 1 and 2 show schematic diagrams of wax cells of different mascara formulations prior to use in the methods of the present disclosure.
Figure 2:
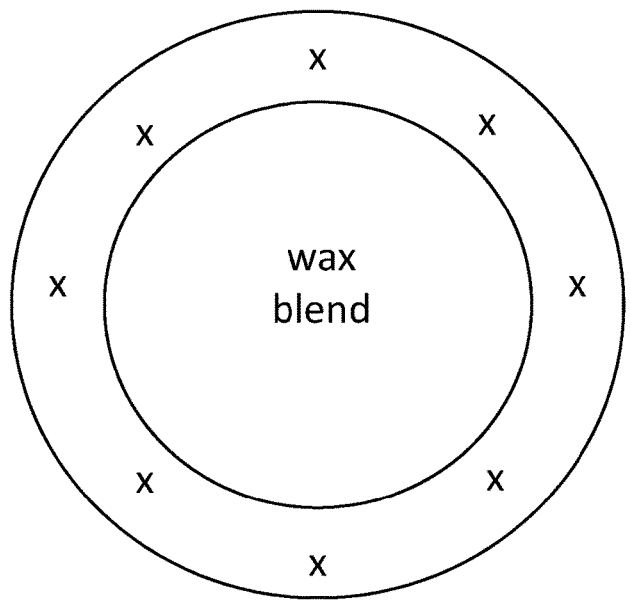

The method of the present invention can be used to prepare cosmetic compositions, specifically, mascara. According to some embodiments, the present disclosure is directed to a method of preparing a cosmetic composition, the method comprising: providing a first mascara formulation having at least one first wax contained therein; providing a second mascara formulation having at least one second wax contained therein, the at least one second wax having a different melting point than that of the at least one first wax; and mixing together the first mascara formulation and the second mascara formulation at a temperature below the melting points of both the at least one first wax and the at least one second wax. In some aspects, one of the first and second mascara formulations has a higher viscosity than the other of the first and second mascara formulations. It has been discovered that the combination of these rheologically different formulas yields an improved and balanced mascara composition that has the characteristics of two different types of mascara formulations. In addition, mixing together the first and second mascara formulations results in a cosmetic composition with a different texture than would be obtained by preparing a cosmetic compositions directly from the component ingredients being mixed together initially.

In some aspects, the first and second mascara formulations are mixed at a temperature below the melting points of all ingredients contained within the first and second mascara formulations.

In some aspects, each of the first and second mascara formulations contains a water-in-oil emulsifier and an oil-in-water emulsifier.

Suitable water-in-oil emulsifiers include, but are not limited to one or more of, polyglyceryl-3-rice branate, cetearyl alcohol, polyglyceryl-10 stearate, polyglyceryl-6 stearate, hydroxypropyl guar, cetearyl alcohol, glyceryl stearate, PEG-30 dipolyhydroxystearate, PEG-40 stearate, cetearet-20, 165-PEG-100 stearate, and glyceyl stearate. In some aspects, the water-in-oil emulsifier may be present in a mascara formulation at a level of 1-20% by weight, such as 1-18, 1-15, 1-12, 1-10, 1-8, 1-5, 1-3, 3-20, 3-18, 3-15, 3-12, 3-10, 3-8, 3-5, 5-20, 5-18, 5-15, 5-12, 5-10, 5-8, 8-20, 8-18, 8-15, 8-12, 8-10, 10-20, 10-18, 10-15, 10-12, 12-20, 12-18, 12-15, 15-20, 15-18, 18-20, 1, 2, 3, 4, 5, 6, 7, 8, 9, 10, 11, 12, 13, 14, 15, 16, 17, 18, 19, or 20% by weight, or any integer or subrange in between.

Suitable oil-in-water emulsifiers include, but are not limited to, one or more of stearic acid with aminomethyl propandiol, stearic acid with sodium hydroxide, GMS, GMS-SE, and potassium cetyl phosphate. In some aspects, the oil-in-water emulsifier may be present in a mascara formulation at a level of 0.5-15% by weight, such as 0.5-12, 0.5-10, 0.5-8, 0.5-5, 0.5-3, 0.5-1, 1-15, 1-12, 1-10, 1-8, 1-5, 1-3, 3-15, 3-12, 3-10, 3-8, 3-5, 5-15, 5-12, 5-10, 5-8, 8-15, 8-12, 8-10, 10-15, 10-12, 12-15, 0.5, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, or 14.5% by weight, or any integer or subrange in between.

In some aspects, the water-in-oil emulsifier in each of the first and second mascara formulations is independently one or more of polyglyceryl-3-rice branate, cetearyl alcohol, polyglyceryl-10 stearate, polyglyceryl-6 stearate, hydroxypropyl guar, cetearyl alcohol, glyceryl stearate, PEG-30 dipolyhydroxystearate, PEG-40 stearate, cetearet-20, 165-PEG-100 stearate, and glyceyl stearate.

In some aspects, the oil-in-water emulsifier in each of the first and second mascara formulations is independently one or more of stearic acid with aminomethyl propandiol, stearic acid with sodium hydroxide, GMS, GMS-SE, and potassium cetyl phosphate.

In some aspects, the first mascara formulation contains both a water-in-oil emulsifier and an oil-in-water emulsifier, and the second mascara formulation contains one or more oil-in-water emulsifiers and does not contain a water-in-oil emulsifier.

In some aspects, the water-in-oil emulsifier is one or more of polyglyceryl-3-rice branate, cetearyl alcohol, polyglyceryl-10 stearate, polyglyceryl-6 stearate, hydroxypropyl guar, cetearyl alcohol, glyceryl stearate, PEG-30 dipolyhydroxystearate, PEG-40 stearate, cetearet-20, 165-PEG-100 stearate, or glyceyl stearate.

In some aspects, the water-in-oil emulsifier is PEG-30-dipolyhydroxystearate.

In some aspects, the oil-in-water emulsifier in each of the first and second mascara formulations is independently one or more of stearic acid with aminomethyl propandiol, stearic acid with sodium hydroxide, GMS, GMS-SE, and potassium cetyl phosphate.

In some aspects, the oil-in-water emulsifier in the first mascara formulation is GMS-SE, and the one or more oil-in-water emulsifiers in the second mascara formulation is stearic acid with aminomethyl propandiol or GMS, or a combination thereof.

In addition, the mascara formulations can contain one or more cosmetically acceptable ingredients. Several types of cosmetically acceptable ingredients, along with examples of the various types, are discussed below. A person of ordinary skill in the art would readily understand which cosmetically acceptable ingredients to use depending on the desired product. Importantly, while several types of exemplary cosmetically acceptable ingredients are discussed herein, the mascara formulations do not necessarily contain type of cosmetically acceptable ingredient discussed. Further, the mascara formulations may contain other types of ingredients other than those discussed. Although specific examples of the various types of cosmetically acceptable ingredients are discussed, other cosmetically acceptable ingredients can also be used. The amounts of such ingredients can range from 0.0001% to 99.9% by weight or volume of either or both of the mascara formulations, or any integer or range in between as disclosed in other sections of this specification, which are incorporated into this paragraph by reference.

The mascara formulations can contain one or more waxes, for example, hydrogenated olive esters, joba wax, rice wax, carnauba wax, candelilla wax, beeswax, lanolin wax, orange peel wax, Chinese insect wax, ouricury wax, cork fiber wax, sugar cane wax, Japan wax, sumach wax, montan wax, microcrystalline waxes, paraffins, polyethylene waxes, methicones, such as methicone and C1-C45 alkyl, phenyl, and mixed C1-C45 alkyl and phenyl methicones, dimethicones, such as dimethicone, C1-C45 alkyl, and mixed C1-C45 alkyl and phenyl dimethicones, and simethicones. In some aspects, the one or more waxes may be present in a mascara formulation at a level of 2-30% by weight, such as 2-25, 2-20, 2-15, 2-12, 2-10, 2-8, 2-5, 5-30, 5-25, 5-20, 5-15, 5-12, 5-10, 5-8, 8-30, 8-25, 8-20, 8-15, 8-12, 8-10, 10-30, 10-25, 10-20, 10-15, 10-12, 12-30, 12-25, 12-20, 12-15, 15-30, 15-25, 15-20, 20-30, 20-25, 25-30, 2, 3, 4, 5, 6, 7, 8, 9, 10, 11, 12, 13, 14, 15, 16, 17, 18, 19, 20, 21, 22, 23, 24, 25, 26, 27, 28, 29, or 30% by weight, or any integer or subrange in between.

In some aspects, the one or more waxes in each of the mascara formulations are independently selected from hydrogenated olive esters, joba wax, rice wax, carnauba wax, candelilla wax, beeswax, lanolin wax, orange peel wax, Chinese insect wax, ouricury wax, cork fiber wax, sugar cane wax, Japan wax, sumach wax, montan wax, microcrystalline waxes, paraffins, polyethylene waxes, methicones, dimethicones, and simethicones.

In some aspects, the one or more waxes in each of the mascara formulations are independently selected from hydrogenated olive esters, beeswax, and carnauba wax.

The mascara formulations can contain also one or more gums, for example acacia gums, such as gum acacia, Senegal gum, gum arabic, gum ghatti, gum karay, gum tragacanth, guar gum, guar hydroxypropyl ammonium chloride, xanthan gum, gellan gum, and mixtures thereof. In some aspects, the one or more gums may be present in a mascara formulation at a level of 1-10% by weight, such as 1-8, 1-5, 1-3, 1-2, 1-1.5, 1.5-10, 1.5-8, 1.5-5, 1.5-3, 1.5-2, 2-10, 2-8, 2-5, 2-3, 3-10, 3-8, 3-5, 5-10, 5-8, 8-10, 1, 1.5, 2, 2.5, 3, 3.5, 4, 4.5, 5, 5.5, 6, 6.5, 7, 7.5, 8, 8.5, 9, 9.5, or 10% by weight, or any integer or subrange in between.

The mascara formulations can contain one or more cellulose polymers, such as cellulose, sodium or potassium carboxymethyl cellulose, hydroxyethyl cellulose, ethyl cellulose, hydroxypropyl cellulose, sulfated cellulose, hydroxypropylmethyl cellulose, microcrystalline cellulose, and mixtures thereof. In some aspects, the one or more cellulose polymers may be present in a mascara formulation at a level of 1-10% by weight, such as 1-8, 1-5, 1-3, 1-2, 1-1.5, 1.5-10, 1.5-8, 1.5-5, 1.5-3, 1.5-2, 2-10, 2-8, 2-5, 2-3, 3-10, 3-8, 3-5, 5-10, 5-8, 8-10, 1, 1.5, 2, 2.5, 3, 3.5, 4, 4.5, 5, 5.5, 6, 6.5, 7, 7.5, 8, 8.5, 9, 9.5, or 10% by weight, or any integer or subrange in between.

The mascara formulations can also contain one or more volatile oils, such as paraffins or isoparaffin having from 8 to 16 carbon atoms, isododecane, isodecane, propylene glycol n-butyl ether, ethyl 3-ethoxy propionate, propylglycol methylether acetates, decamethyltetrasiloxane, octatrimethicone, hexatrimethicone, decamethylcyclopeta siloxane, octamethylcyclotetrasiloxane, dodecamethylcyclohexyl siloxane, polydimethyl siloxande (PDMS), and decamethyltetra siloxane. In some aspects, the one or more volatile oils may be present in a mascara formulation at a level of 5-25% by weight, 5-22, 5-20, 5-18, 5-15, 5-12, 5-10, 5-8, 8-25, 8-22, 8-20, 8-18, 8-15, 8-12, 8-10, 10-25, 10-22, 10-20, 10-18, 10-15, 10-12, 12-25, 12-22, 12-20, 12-18, 12-15, 15-25, 15-22, 15-20, 15-18, 18-25, 18-22, 18-20, 20-25, 20-22, 22-25, 5, 6, 7, 8, 9, 10, 11, 12, 13, 14, 15, 16, 17, 18, 19, 20, 21, 22, 23, 24, or 25% by weight, or any integer or subrange in between.

The mascara formulations can contain water. In some aspects, water may be present in a mascara formulation at a level of 45-60% by weight, such as 45-57, 45-55, 45-52, 45-50, 45-47, 47-60, 47-57, 47-55, 47-52, 47-50, 50-60, 50-57, 50-55, 50-52, 52-60, 52-57, 52-55, 55-60, 55-57, 57-60, 45, 46, 47, 48, 49, 49.6, 50, 51, 52, 53, 54, 55, 56, 57, 58, 59, or 60% by weight, or any integer or subrange in between.

The mascara formulations can contain one or more low molecular weight alcohols, for example, ethyl alcohol, propyl alchol, such as n-propyl or isopropyl alcohol, or butyl alcohol, such as n-butyl, isobutyl, sec-butyl or t-butyl alcohol. In some aspects, the one or more low molecular weight alcohols may be denatured. In some aspects, the one or more low molecular weight alcohols may be present in a mascara formulation at a level of 0.1-5% by weight, such as 0.1-4.5, 0.1-4, 0.1-3.5, 0.1-3, 0.1-2.5, 0.1-2, 0.1-1.5, 0.1-1, 0.1-0.8, 0.1-0.5, 0.1-0.2, 0.2-5, 0.2-4.5, 0.2-4, 0.2-3.5, 0.2-3, 0.2-2.5, 0.2-2, 0.2-1.5, 0.2-1, 0.2-0.8, 0.2-0.5, 0.5-5, 0.5-4.5, 0.5-4, 0.5-3.5, 0.5-3, 0.5-2.5, 0.5-2, 0.5-1.5, 0.5-1, 0.5-0.8, 0.8-5, 0.8-4.5, 0.8-4, 0.8-3.5, 0.8-3, 0.8-2.5, 0.8-2, 0.8-1.5, 0.8-1, 1-5, 1-4.5, 1-4, 1-3.5, 1-3, 1-2.5, 1-2, 1-1.5, 1.5-5, 1.5-4.5, 1.5-4, 1.5-3.5, 1.5-3, 1.5-2.5, 1.5-2, 2-5, 2-4.5, 2-4, 2-3.5, 2-3, 2-2.5, 2.5-5, 2.5-4.5, 2.5-4, 2.5-3.5, 2.5-3, 3-5, 3-4.5, 3-4, 3-3.5, 3.5-5, 3.5-4.5, 3.5-4, 4-5, 4-4.5, 4.5-5, 0.1, 0.2, 0.3, 0.4, 0.5, 0.6, 0.7, 0.8, 0.9, 1, 1.5, 2, 2.5, 3, 3.5, 4, 4.5, or 5% by weight, or any integer or subrange in between.

The mascara formulations can contain one or more humectants, for example, polyhydric alcohols, glycerol, glycerin, C1 to C4 alkane glycols, such as butylene propylene, and ethylene glycol, alkylene polyols, hyaluronic acid, urea, sorbitol, 2-pyrrolidone-5-carboxylate salts, such as sodium or potassium salts, collagen, dibutylphthalate, and gelatin. In some aspects, the one or more humectants may be present in a mascara formulation at a level of 0.5-5% by weight, such as, 0.5-4.5, 0.5-4, 0.5-3.5, 0.5-3, 0.5-2.5, 0.5-2, 0.5-1.5, 0.5-1.2, 0.5-1, 0.5-0.8, 0.5-0.6, 0.5-5, 0.6-5, 0.6-4.5, 0.6-4, 0.6-3.5, 0.6-3, 0.6-2.5, 0.6-2, 0.6-1.5, 0.6-1.2, 0.6-1, 0.6-0.8, 0.8-5, 0.8-4.5, 0.8-4, 0.8-3.5, 0.8-3, 0.8-2.5, 0.8-2, 0.8-1.5, 0.8-1.2, 0.8-1, 1-5, 1-4.5, 1-4, 1-3.5, 1-3, 1-2.5, 1-2, 1-1.5, 1-1.2, 1.2-5, 1.2-4.5, 1.2-4, 1.2-3.5, 1.2-3, 1.2-2.5, 1.2-2, 1.2-1.5, 1.5-5, 1.5-4.5, 1.5-4, 1.5-3.5, 1.5-3, 1.5-2.5, 1.5-2, 2-5, 2-4.5, 2-4, 2-3.5, 2-3, 2-2.5, 2.5-5, 2.5-4.5, 2.5-4, 2.5-3.5, 2.5-3, 3-5, 3-4.5, 3-4, 3-3.5, 3.5-5, 3.5-4.5, 3.5-4, 4-5, 4-4.5, 4.5-5, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, or 5% by weight, or any integer or subrange in between.

The mascara formulation can contain one or more fillers, pigments, and colorants, for example, iron oxides, talc, mica, magnesium carbonate, calcium carbonate, magnesium silicate, aluminum magnesium silicate, silica, polyethylene, (meth)acrylate, polystyrene, silk, crystalline cellulose, starch, bismuth oxide, zinc oxide, salts or lakes of aluminun, barium, or calcium, organic dyes, such as FD&C dyes or lakes thereof, and carbon black. The one or more pigments, colorants, or fillers can be treated with one or more hydrophilic polymers, for example, polyethylene glycols and polyquaterniums. The one or more pigments or colorants can be present in solution or as dispersed particles. The one or more pigments or colorants can also be adapted to produce a pearlescent effect. In some aspects, the one or more fillers, pigments, and colorants may be present in a mascara formulation at a level of 0.1-10% by weight, such as 0.1-8, 0.1-5, 0.1-3, 0.1-2, 0.1-1.5, 0.1-1.2, 0.1-1, 0.1-0.8, 0.1-0.5, 0.1-0.3, 0.3-10, 0.3-8, 0.3-5, 0.3-3, 0.3-2, 0.3-1.5, 0.3-1.2, 0.3-1, 0.3-0.8, 0.3-0.5, 0.5-10, 0.5-8, 0.5-5, 0.5-3, 0.5-2, 0.5-1.5, 0.5-1.2, 0.5-1, 0.5-0.8, 0.8-10, 0.8-8, 0.8-5, 0.8-3, 0.8-2, 0.8-1.5, 0.8-1, 1-10, 1-8, 1-5, 1-3, 1-2, 1-1.5, 1-1.2, 1.2-10, 1.2-8, 1.2-5, 1.2-3, 1.2-1.5, 1.5-10, 1.5-8, 1.5-5, 1.5-3, 1.5-2, 2-10, 2-8, 2-5, 2-3, 3-10, 3-8, 3-5, 5-10, 5-8, 8-10, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.5, 2.8, 3, 3.5, 4, 4.5, 5, 5.5, 6, 6.5, 7, 7.5, 8, 8.5, 9, 9.5, or 10% by weight, or any integer or subrange in between.

The mascara formulations can include one or more preservatives, for example parabens, such as methyl, ethyl, propyl, dimethyl, or butyl paraben, phenoxy ethanol, ethylhexyl glycerin, sodium dehydroacetate, potassim sorbate, imidazoleidinyl urea, capryl glycol, hexylene glycol, pheoxy ethanol, p-hydroxy benzoate and esters thereof. The one or more preservatives can be present in an amount sufficient to prevent or inhibit the growth of microbes. In some aspects, the one or more preservatives may be present in a mascara formulation at a level of 0.01-5% by weight, such as 0.01-4.5, 0.01-4, 0.01-3.5, 0.01-3, 0.01-2.5, 0.01-2, 0.01-1.5, 0.01-1, 0.01-0.8, 0.01-0.5, 0.01-0.2, 0.01-0.1, 0.01-0.08, 0.01-0.05, 0.01-0.03, 0.03-5, 0.03-4.5, 0.03-4, 0.03-3.5, 0.03-3, 0.03-2.5, 0.03-2, 0.03-1.5, 0.03-1, 0.03-0.8, 0.03-0.5, 0.03-0.2, 0.03-0.1, 0.03-0.08, 0.03-0.05, 0.05-5, 0.05-4.5, 0.05-4, 0.05-3.5, 0.05-3, 0.05-2.5, 0.05-2, 0.05-1.5, 0.05-1, 0.05-0.8, 0.05-0.5, 0.05-0.2, 0.05-0.1, 0.05-0.08, 0.08-5, 0.08-4.5, 0.08-4, 0.08-3.5, 0.08-3, 0.08-2.5, 0.08-2, 0.08-1.5, 0.08-1, 0.08-0.8, 0.08-0.5, 0.08-0.2, 0.08-0.1, 0.1-5, 0.1-4.5, 0.1-4, 0.1-3.5, 0.1-3, 0.1-2.5, 0.1-2, 0.1-1.5, 0.1-1, 0.1-0.8, 0.1-0.5, 0.1-0.2, 0.2-5, 0.2-4.5, 0.2-4, 0.2-3.5, 0.2-3, 0.2-2.5, 0.2-2, 0.2-1.5, 0.2-1, 0.2-0.8, 0.2-0.5, 0.5-5, 0.5-4.5, 0.5-4, 0.5-3.5, 0.5-3, 0.5-2.5, 0.5-2, 0.5-1.5, 0.5-1, 0.5-0.8, 0.8-5, 0.8-4.5, 0.8-4, 0.8-3.5, 0.8-3, 0.8-2.5, 0.8-2, 0.8-1.5, 1-5, 1-4.5, 1-4, 1-3.5, 1-3, 1-2.5, 1-2, 1-1.5, 1.5-5, 1.5-4.5, 1.5-4, 1.5-3.5, 1.5-3, 1.5-2.5, 1.5-2, 2-5, 2-4.5, 2-4, 2-3.5, 2-3, 2-2.5, 2.5-5, 2.5-4.5, 2.5-4, 2.5-3.5, 2.5-3, 3-5, 3-4.5, 3-4, 3-3.5, 3.5-5, 3.5-4.5, 3.5-4, 4-5, 4-4.5, 4.5-5, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.5, 2, 2.5, 3, 3.5, 4, 4.5, or 5% by weight, or any integer or subrange in between.

The mascara formulations can also contain one or more film forming agents, for example, waxes, such as the waxes discussed above, polyolefins, ethylene vinyl acetate, dimethocone gum, polyterpenes, silionce resins, such as trimethylsiloxy silicate, vinylpyrrolidone/eicosene copolymer, vinylpyrrolidone/hexadecene copolymer, vinylpyrrolidone/ vinyl acetate copolymer, vinylpyrrolidone/(alk)acrylate copolymer, for example copolymers of vinyl pyrrolidone with one or more of ethacrylate, methacrylate, acrylate, acrylic acid, vinylpyrrolidone/styrene copolymer, ethyl cellulose, propyl cellulose, polyalkylenes, such as polymers or copolymers of C2 to C20 polyalkylenes or polybutylene, polyvinylpyrrolidone, and partially or wholly butylated polyvinylpyrrolidone. The one or more film forming agents can be present in an amount sufficient to ensure that the cosmetic composition forms an acceptable film, for example, on the skin or on one or more keratinous fibers, such as the hair, and often the eyelashes or eyebrows. In some aspects, the one or more film forming agents may be present in a mascara formulation at a level of 0.5-2% by weight, such as 0.5-1.8, 0.5-1.5, 0.5-1.3, 0.5-1, 0.5-0.8, 0.5-0.6, 0.6-2, 0.6-1.8, 0.6-1.5, 0.6-1.3, 0.6-1, 0.6-0.8, 0.8-2, 0.8-1.8, 0.8-1.5, 0.8-1.3, 0.8-1, 1-2, 1-1.8, 1-1.5, 1-1.3, 1.3-2, 1.3-1.8, 1.3-1.5, 1.5-2, 1.5-1.8, 1.8-2, 0.5, 0.6, 0.7, 0.8, 0.9, 1, 1.1, 1.2, 1.3, 1.4, 1.5, 1.6, 1.7, 1.8, 1.9, or 2% by weight, or any integer or subrange in between.

The mascara formulations can include one or more structuring agents, for example, stearic acid, palmitic acid, stearyl alcohol, cetyl alcohol, polyethylene glycol ethers of stearyl alcohol, polyethylene glycol ethers of cetyl alcohol, behenyl alcohol, steareth-2 (i.e., a polyethylene glycol ether of stearyl alcohol with an average of about 2 ethylene oxide units per stearyl alcohol unit), acrylic acid/ethyl acrylate copolymers, carbomers, carboxyvinyl polymers, water-soluble polymers of polyalkenyl polyether polymer of acrylic acid crosslinked with from 0.75% to 2.0% of polyallyl sucrose or polyallyl pentaerythritol, lic acid crosslinked with about 1% of polyallyl ether of sucrose, acrylates/10-30 alkyl acrylate cross-polymers, waxes, such as the waxes discussed above, Fischer-Tropsch waxes, silicone waxes, C24-C45 methicones, saturated polyglucosides, trihydroxystearin, hydroxy cellulose, hycroxymethyl cellulose, ethy cellulose, and methyl cellulose. The one or more structuring agents can be present in an amount sufficient to ensure that the cosmetic composition, when applied to the skin or to one or more keratinous fibers, such as the hair, and often the eyelashes or eyebrows, maintains a sufficient structure to obtain a cosmetically desirable effect. In some aspects, the one or more structuring agents may be present in a mascara formulation at a level of 0.1-8% by weight, such as 0.1-5, 0.1-3, 0.1-1, 0.1-0.8, 0.1-0.5, 0.1-0.2, 0.2-8, 0.2-5, 0.2-3, 0.2-1, 0.2-0.8, 0.2-0.5, 0.5-8, 0.5-5, 0.5-3, 0.5-1, 0.5-0.8, 0.8-8, 0.8-5, 0.8-3, 0.8-1, 1-8, 1-5, 1-3, 3-8, 3-5, 5-8, 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, or 8% by weight, or any integer or subrange in between.

The mascara formulations can include one or more fragrances. The one or more fragrances may be present in an amount sufficient to impart a pleasing or commercially acceptable odor. In some aspects, the one or more fragrances may be present in a mascara formulation at a level of 0.01-5% by weight, such as 0.01-4.5, 0.01-4, 0.01-3.5, 0.01-3, 0.01-2.5, 0.01-2, 0.01-1.5, 0.01-1, 0.01-0.8, 0.01-

0.5, 0.01-0.2, 0.01-0.1, 0.01-0.08, 0.01-0.05, 0.01-0.03, 0.03-5, 0.03-4.5, 0.03-4, 0.03-3.5, 0.03-3, 0.03-2.5, 0.03-2, 0.03-1.5, 0.03-1, 0.03-0.8, 0.03-0.5, 0.03-0.2, 0.03-0.1, 0.03-0.08, 0.03-0.05, 0.05-5, 0.05-4.5, 0.05-4, 0.05-3.5, 0.05-3, 0.05-2.5, 0.05-2, 0.05-1.5, 0.05-1, 0.05-0.8, 0.05-0.5, 0.05-0.2, 0.05-0.1, 0.05-0.08, 0.08-5, 0.08-4.5, 0.08-4, 0.08-3.5, 0.08-3, 0.08-2.5, 0.08-2, 0.08-1.5, 0.08-1, 0.08-0.8, 0.08-0.5, 0.08-0.2, 0.08-0.1, 0.1-5, 0.1-4.5, 0.1-4, 0.1-3.5, 0.1-3, 0.1-2.5, 0.1-2, 0.1-1.5, 0.1-1, 0.1-0.8, 0.1-0.5, 0.1-0.2, 0.2-5, 0.2-4.5, 0.2-4, 0.2-3.5, 0.2-3, 0.2-2.5, 0.2-2, 0.2-1.5, 0.2-1, 0.2-0.8, 0.2-0.5, 0.5-5, 0.5-4.5, 0.5-4, 0.5-3.5, 0.5-3, 0.5-2.5, 0.5-2, 0.5-1.5, 0.5-1, 0.5-0.8, 0.8-5, 0.8-4.5, 0.8-4, 0.8-3.5, 0.8-3, 0.8-2.5, 0.8-2, 0.8-1.5, 0.8-1, 1-5, 1-4.5, 1-4, 1-3.5, 1-3, 1-2.5, 1-2, 1-1.5, 1.5-5, 1.5-4.5, 1.5-4, 1.5-3.5, 1.5-3, 1.5-2.5, 1.5-2, 2-5, 2-4.5, 2-4, 2-3.5, 2-3, 2-2.5, 2.5-5, 2.5-4.5, 2.5-4, 2.5-3.5, 2.5-3, 3-5, 3-4.5, 3-4, 3-3.5, 3.5-5, 3.5-4.5, 3.5-4, 4-5, 4-4.5, 4.5-5, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.5, 2, 2.5, 3, 3.5, 4, 4.5, or 5% by weight, or any integer or subrange in between.

The mascara formulations may also include one or more fibers, such as polyester fibers, rayon fibers, nylon fibers, and polyamide fibers. When the composition is designed for application to one or more keratinous fibers, for example the eyebrows or eyelashes, the one or more fibers may be present in an amount sufficient to achieve a fiber-lengthening effect, such as a lash-lengthening effect. In some aspects, the one or more fibers may be present in a mascara formulation at a level of 0.01-5% by weight, such as 0.01-4.5, 0.01-4, 0.01-3.5, 0.01-3, 0.01-2.5, 0.01-2, 0.01-1.5, 0.01-1, 0.01-0.8, 0.01-0.5, 0.01-0.2, 0.01-0.1, 0.01-0.08, 0.01-0.05, 0.01-0.03, 0.03-5, 0.03-4.5, 0.03-4, 0.03-3.5, 0.03-3, 0.03-2.5, 0.03-2, 0.03-1.5, 0.03-1, 0.03-0.8, 0.03-0.5, 0.03-0.2, 0.03-0.1, 0.03-0.08, 0.03-0.05, 0.05-5, 0.05-4.5, 0.05-4, 0.05-3.5, 0.05-3, 0.05-2.5, 0.05-2, 0.05-1.5, 0.05-1, 0.05-0.8, 0.05-0.5, 0.05-0.2, 0.05-0.1, 0.05-0.08, 0.08-5, 0.08-4.5, 0.08-4, 0.08-3.5, 0.08-3, 0.08-2.5, 0.08-2, 0.08-1.5, 0.08-1, 0.08-0.8, 0.08-0.5, 0.08-0.2, 0.08-0.1, 0.1-5, 0.1-4.5, 0.1-4, 0.1-3.5, 0.1-3, 0.1-2.5, 0.1-2, 0.1-1.5, 0.1-1, 0.1-0.8, 0.1-0.5, 0.1-0.2, 0.2-5, 0.2-4.5, 0.2-4, 0.2-3.5, 0.2-3, 0.2-2.5, 0.2-2, 0.2-1.5, 0.2-1, 0.2-0.8, 0.2-0.5, 0.5-5, 0.5-4.5, 0.5-4, 0.5-3.5, 0.5-3, 0.5-2.5, 0.5-2, 0.5-1.5, 0.5-1, 0.5-0.8, 0.8-5, 0.8-4.5, 0.8-4, 0.8-3.5, 0.8-3, 0.8-2.5, 0.8-2, 0.8-1.5, 0.8-1, 1-5, 1-4.5, 1-4, 1-3.5, 1-3, 1-2.5, 1-2, 1-1.5, 1.5-5, 1.5-4.5, 1.5-4, 1.5-3.5, 1.5-3, 1.5-2.5, 1.5-2, 2-5, 2-4.5, 2-4, 2-3.5, 2-3, 2-2.5, 2.5-5, 2.5-4.5, 2.5-4, 2.5-3.5, 2.5-3, 3-5, 3-4.5, 3-4, 3-3.5, 3.5-5, 3.5-4.5, 3.5-4, 4-5, 4-4.5, 4.5-5, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.5, 2, 2.5, 3, 3.5, 4, 4.5, or 5% by weight, or any integer or subrange in between.

The mascara formulations can also include one or more hair active agents, such as straighteners, conditioners, hair growth agents, for example one or more of progesterones and progestamides, curling compounds, amino acids, proteins, carageenen, algae extract, wheat flour lipids, and dyes. In some aspects, the one or more hair active agents may be present in a mascara formulation at a level of 0.01-10% by weight, such as 0.01-8, 0.01-5, 0.01-3, 0.01-1, 0.01-0.8, 0.01-0.5, 0.01-0.3, 0.01-0.1, 0.01-0.08, 0.01-0.05, 0.01-0.03, 0.03-10, 0.03-8, 0.03-5, 0.03-3, 0.03-1, 0.03-0.8, 0.03-0.5, 0.03-0.3, 0.03-0.1, 0.03-0.08, 0.03-0.05, 0.05-10, 0.05-8, 0.05-5, 0.05-3, 0.05-1, 0.05-0.8, 0.05-0.5, 0.08-0.3, 0.08-0.1, 0.1-10, 0.1-8, 0.1-5, 0.1-3, 0.1-1, 0.1-0.8, 0.1-0.5, 0.1-0.3, 0.3-10, 0.3-8, 0.3-5, 0.3-3, 0.3-1, 0.3-0.8, 0.3-0.5, 0.5-10, 0.5-8, 0.5-5, 0.5-3, 0.5-1, 0.5-0.8, 0.8-10, 0.8-8, 0.8-5, 0.8-3, 0.8-1, 1-10, 1-8, 1-5, 1-3, 3-10, 3-8, 3-5, 5-10, 5-8, 8-10, 0.01, 0.02. 0.03, 0.04, 0.05, 0.06, 0.07, 0.08, 0.09, 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, or 10% by weight, or any integer or subrange in between.

The mascara formulations, as well as the cosmetic composition resulting from mixing of the mascara formulations, can be a liquid at room temperature, and can include dispersed or dissolved particles.

The mascara formulations, as well as the cosmetic composition resulting from mixing of the mascara formulations, can be provided in a container, for example, a glass or plastic container, which can be, for example, a bottle, hard tube, squeezable tube, or pouch. The container can be provided with an applicator, such as a brush or pen applicator. The applicator can be integrated with one or more parts of the container. For example, a brush applicator may be integrated with the top of a bottle. The applicator can also be provided separately.

A method of using the cosmetic composition can involve treating keratinous fibers by applying the composition to keratinous fibers. Keratinous fibers can include, for example, hair, such as human hair. The human hair can be, for example, hair of the head, eyelashes, or eyebrows.

The mascara formulations to be mixed together, as well as the cosmetic composition resulting from mixing of the mascara formulations, can be made by admixing the components, for example one or more of the components discussed above, in appropriate amounts and in appropriate sub-combinations before making the final product.

The mascara formulations may be mixed together by any suitable means known to those of ordinary skill in the art.

The viscosity of the resulting cosmetic composition may be measured by any suitable means known to those of ordinary skill in the art, such as using a viscometer. The melting points of waxes or other ingredients may be measured by any suitable means known to those of ordinary skill in the art. Alternatively, the melting points of some waxes or other ingredients may be known in the art.

The following are examples of different mascara formulations followed by Examples 1-3 showing exemplary percentages of each mixed together according to the methods of the present disclosure.

Phases A (wax phase) and B (water phase) were heated separately to 85° C. Phase B was then added to Phase A, and the resulting mixture was homogenized for 15 minutes. The homogenized mixture was then cooled down to 35° C. under mixing.

Mascara formulation #1:

| Description | Quantity (weight %) | Melting Point (° C.) |
|---|---|---|
| Phase A | | |
| VP/Eicosene copolymer | 2.00 | 40 |
| PEG-30 dipolyhydroxystearate (PEG-30 DPHS) | 2.00 | 38 |
| GmS SE | 14.00 | 58 |
| Cyclopentasiloxane | 7.00 | |
| Polybutene | 2.00 | |
| Hydrogenated olive esters | 6.00 | 58 |
| Phase B | | |
| Gum acacia | 3.00 | |
| Iron oxide | 8.00 | |
| Methylparaben | 0.20 | |
| Phenoxyethanol | 0.80 | |
| Acqua | 55.00 | |
| TOTAL | 100.00 | |

Mascara formulation #2:

| Description | Quantity (weight %) | Melting Point (° C.) |
|---|---|---|
| Phase A | | |
| VP/Eicosene copolymer | 2.00 | 40 |
| Stearic acid | 7.00 | 62 |
| Beeswax | 10.00 | 63 |
| Cyclopentasiloxane | 4.00 | |
| Polybutene | 2.00 | |
| GMS | 1.00 | 60 |
| Synthetic beeswax | 3.00 | 80 |
| Carnuaba wax | 3.00 | 80 |
| Phase B | | |
| Gum acacia | 3.00 | |
| Aminomethylpropandiol | 1.00 | |
| Iron oxide | 8.00 | |
| Methylparaben | 0.20 | |
| Phenoxyethanol | 0.80 | |
| Acqua | 55.00 | |
| TOTAL | 100.00 | |

Mascara formulation #3:

| Description | Quantity (weight %) |
|---|---|
| Phase A | |
| VP/Eicosene copolymer | 2.00 |
| Stearic acid | 7.00 |
| Beeswax | 10.00 |
| Cyclopentasiloxane | 4.00 |
| Polybutene | 2.00 |
| Carnuaba wax | 6.00 |
| Phase B | |
| Gum acacia | 3.00 |
| Aminomethylpropandiol | 2.00 |
| Iron oxide | 8.00 |
| Methylparaben | 0.20 |
| Phenoxyethanol | 0.80 |
| Acqua | 55.00 |
| TOTAL | 100.00 |

Mascara formulation #4:

| Description | Quantity (weight %) | Melting Point (° C.) |
|---|---|---|
| Phase A | | |
| VP/Eicosene copolymer | 2.00 | 40 |
| Stearic acid | 7.00 | 63 |
| Beeswax | 12.00 | 63 |
| Cyclopentasiloxane | 4.00 | |
| Polybutene | 2.00 | |
| Carnuaba wax | 9.00 | |
| Phase B | | |
| Gum acacia | 3.00 | |
| Aminomethylpropandiol | 2.40 | |
| Iron oxide | 8.00 | |
| Methylparaben | 0.20 | |
| Phenoxyethanol | 0.80 | |
| Acqua | 49.60 | |
| TOTAL | 100.00 | |

EXAMPLE 1

| Mascara Formulation | Amount (weight %) |
|---|---|
| #1 | 50 |
| #2 | 50 |

EXAMPLE 2

| Mascara Formulation | Amount (weight %) |
|---|---|
| #1 | 40 |
| #2 | 30 |
| #3 | 30 |

EXAMPLE 3

| Mascara Formulation | Amount (weight %) |
|---|---|
| #1 | 80 |
| #2 | 20 |

EXAMPLE 4

| Mascara Formulation | Amount (weight %) |
|---|---|
| #2 | 50 |
| #4 | 50 |

Mascara formulation #1 contains both oil-in-water and water-in-oil emulsifiers and would be considered too thick for use on its own. However, by blending #1 with either #2 and/or #3 at 35° C. (i.e., below the melting point of their respective wax components) at the relative percentages of each indicated in the examples, a very balanced mascara is produced.

Mascara formulation #2 is an example of a light textured mascara with only oil-in-water emulsifiers. Mascara formulation #4 is an example of a heavy, almost too dry mascara. But by mixing these below their melting points, a balanced mascara is produced.

As used herein, the term "about" is defined to being close to as understood by one of ordinary skill in the art. In one non-limiting embodiment, the term "about" is defined to be within 10%, preferably within 5%, more preferably within 1%, and most preferably within 0.5%.

While the aspects described herein have been described in conjunction with the example aspects outlined above, various alternatives, modifications, variations, improvements, and/or substantial equivalents, whether known or that are or may be presently unforeseen, may become apparent to those having at least ordinary skill in the art. Accordingly, the example aspects, as set forth above, are intended to be illustrative, not limiting. Various changes may be made without departing from the spirit and scope of the disclosure. Therefore, the disclosure is intended to embrace all known or later-developed alternatives, modifications, variations, improvements, and/or substantial equivalents.

Reference to an element in the singular is not intended to mean "one and only one" unless specifically so stated, but rather "one or more." All structural and functional equivalents to the elements of the various aspects described throughout this disclosure that are known or later come to be known to those of ordinary skill in the art are expressly incorporated herein by reference. Moreover, nothing disclosed herein is intended to be dedicated to the public.

Further, the word "example" is used herein to mean "serving as an example, instance, or illustration." Any aspect described herein as "example" is not necessarily to be construed as preferred or advantageous over other aspects. Unless specifically stated otherwise, the term "some" refers to one or more. Combinations such as "at least one of A, B, or C," "at least one of A, B, and C," and "A, B, C, or any combination thereof" include any combination of A, B, and/or C, and may include multiples of A, multiples of B, or multiples of C. Specifically, combinations such as "at least one of A, B, or C," "at least one of A, B, and C," and "A, B, C, or any combination thereof" may be A only, B only, C only, A and B, A and C, B and C, or A and B and C, where any such combinations may contain one or more member or members of A, B, or C.

Moreover, all references throughout this application, for example patent documents including issued or granted patents or equivalents; patent application publications; and non-patent literature documents or other source material; are hereby incorporated by reference herein in their entireties, as though individually incorporated by reference.

What is claimed is:

1. A method of preparing a cosmetic composition, the method comprising:
    providing a first mascara formulation having at least one first wax contained therein;
    providing a second mascara formulation having at least one second wax contained therein, the at least one second wax having a different melting point than that of the at least one first wax; and
    mixing together the first mascara formulation and the second mascara formulation at a temperature below the melting points of both the at least one first wax and the at least one second wax, wherein
    the first mascara formulation contains both a water-in-oil emulsifier and an oil-in-water emulsifier, and
    the second mascara formulations contains one or more oil-in-water emulsifiers and does not contain a water-in-oil emulsifier.

2. The method of claim 1, wherein one of the first and second mascara formulations has a higher viscosity than the other of the first and second mascara formulations.

3. The method of claim 1, wherein the water-in-oil emulsifier is one or more of polyglyceryl-3-rice branate, cetearyl alcohol, polyglyceryl-10 stearate, polyglyceryl-6 stearate, hydroxypropyl guar, glyceryl stearate, PEG-30 dipolyhydroxystearate, PEG-40 stearate, cetearet-20, 165-PEG-100 stearate, or glyceyl stearate.

4. The method of claim 3, wherein the water-in-oil emulsifier is PEG-30-dipolyhydroxystearate.

5. The method of claim 1, wherein the oil-in-water emulsifier in each of the first and second mascara formulations is independently one or more of stearic acid with aminomethyl propandiol, stearic acid with sodium hydroxide, GMS, GMS-SE, and potassium cetyl phosphate.

6. The method of claim 5, wherein
    the oil-in-water emulsifier in the first mascara formulation is GMS-SE, and
    the one or more oil-in-water emulsifiers in the second mascara formulation is stearic acid with aminomethyl propandiol or GMS, or a combination thereof.

7. The method of claim 1, wherein each of the first and second waxes are independently selected from hydrogenated olive esters, joba wax, rice wax, carnauba wax, candelilla wax, beeswax, lanolin wax, orange peel wax, Chinese insect wax, ouricury wax, cork fiber wax, sugar cane wax, Japan wax, sumach wax, montan wax, microcrystalline waxes, paraffins, polyethylene waxes, methicones, dimethicones, and simethicones.

8. The method of claim 1, wherein each of the first and second waxes are independently selected from hydrogenated olive esters, beeswax, and carnauba wax.

9. The method of claim 1,
    wherein the first mascara formulation comprises:
        a phase A comprising:
            2.00 weight % of VP/Eicosene copolymer,
            2.00 weight % of PEG-30 DPHS,
            14.00 weight % of GmS SE,
            7.00 weight % of cyclopentasiloxane,
            2.00 weight % of polybutene, and
            6.00 weight % of hydrogenated olive esters; and
        a phase B comprising:
            3.00 weight % of gum acacia,
            8.00 weight % of iron oxide,
            0.20 weight % of methylparaben,
            0.80 weight % of phenoxyethanol, and
            55.00 weight % of water; and
        wherein each weight % of phase A and B is with respect to the total weight of the first formulation; and
    the second mascara formulation comprises:
        a phase A comprising:
            2.00 weight % of VP/Eicosene copolymer,
            7.00 weight % of stearic acid,
            10.00 weight % of beeswax,
            4.00 weight % of cyclopentasiloxane,
            2.00 weight % of polybutene,
            1.00 weight % of GMS,
            3.00 weight % of synthetic beeswax,
            3.00 weight % of carnauba wax; and
        a phase B comprising:
            3.00 weight % of gum acacia,
            1.00 weight % of aminomethylpropandiol,
            8.00 weight % of iron oxide,
            0.20 weight % of methylparaben,
            0.80 weight % of phenoxyethanol,
            55.00 weight % of water, and
        wherein each weight % of phase A and B is with respect to the total weight of the second formulation.

10. The method of claim 9, further comprising:
    providing a third mascara formulation having at least one third wax contained therein, the at least one third wax having a different melting point than that of the at least one first wax; and
    mixing together the first and second mascara formulations with the third mascara formulation at a temperature below the melting points of both the at least one first wax and the at least one third wax.

11. The method of claim 10, wherein the third mascara formulation comprises:
    a phase A comprising:
        2.00 weight % of VP/Eicosene copolymer,
        7.00 weight % of stearic acid,
        10.00 weight % of beeswax,
        4.00 weight % of cyclopentasiloxane, 2.00 weight % of polybutene,
6.00 weight % of carnauba wax; and
a phase B comprising:
   3.00 weight % of gum acacia,
   2.00 weight % of aminomethylpropandiol,
   8.00 weight % of iron oxide,
   0.20 weight % of methylparaben,
   0.80 weight % of phenoxyethanol,
   55.00 weight % of water, and
wherein each weight % of phase A and B is with respect to the total weight of the third formulation.

12. A method of preparing a cosmetic composition, the method comprising:
providing a first mascara formulation having at least one first wax contained therein;
providing a second mascara formulation having at least one second wax contained therein, the at least one second wax having a different melting point than that of the at least one first wax; and
mixing together the first mascara formulation and the second mascara formulation at a temperature below the melting points of both the at least one first wax and the at least one second wax,
wherein the first mascara formulation comprises:
   a phase A comprising:
      2.00 weight % of VP/Eicosene copolymer,
      7.00 weight % of stearic acid,
      10.00 weight % of beeswax,
      4.00 weight % of cyclopentasiloxane,
      2.00 weight % of polybutene,
      1.00 weight % of GMS,
      3.00 weight % of synthetic beeswax, and
      3.00 weight % of carnauba wax; and
   a phase B comprising:
      3.00 weight % of gum acacia,
      1.00 weight % of aminomethylpropandiol,
      8.00 weight % of iron oxide,
      0.20 weight % of methylparaben,
      0.80 weight % of phenoxyethanol,
      55.00 weight % of water, and
   wherein each weight % of phase A and B is with respect to the total weight of the first formulation; and
the second mascara formulation comprises:
   a phase A comprising:
      2.00 weight % of VP/Eicosene copolymer,
      7.00 weight % of stearic acid,
      12.00 weight % of beeswax,
      4.00 weight % of cyclopentasiloxane,
      2.00 weight % of polybutene,
      9.00 weight % of carnauba wax; and
   a phase B comprising:
      3.00 weight % of gum acacia,
      2.40 weight % of aminomethylpropandiol,
      8.00 weight % of iron oxide,
      0.20 weight % of methylparaben,
      0.80 weight % of phenoxyethanol,
      49.60 weight % of water, and
   wherein each weight % of phase A and B is with respect to the total weight of the second formulation.

* * * * *